(12) United States Patent
Wampler

(10) Patent No.: US 9,173,985 B2
(45) Date of Patent: Nov. 3, 2015

(54) TOTAL ARTIFICIAL HEART

(71) Applicant: Richard Wampler, Loomis, CA (US)

(72) Inventor: Richard Wampler, Loomis, CA (US)

(73) Assignee: OREGONHEART, INC., Portland, OR (US)

( * ) Notice: Subject to any disclaimer, the term of this patent is extended or adjusted under 35 U.S.C. 154(b) by 158 days.

(21) Appl. No.: 14/083,752

(22) Filed: Nov. 19, 2013

(65) Prior Publication Data
US 2014/0155998 A1    Jun. 5, 2014

Related U.S. Application Data

(63) Continuation of application No. 12/960,129, filed on Dec. 3, 2010, now Pat. No. 8,608,798.

(60) Provisional application No. 61/266,405, filed on Dec. 3, 2009.

(51) Int. Cl.
*A61M 1/10*    (2006.01)
*A61M 1/12*    (2006.01)

(52) U.S. Cl.
CPC ............... *A61M 1/101* (2013.01); *A61M 1/122* (2013.01)

(58) Field of Classification Search
CPC ........................................................ A61M 1/10
USPC ........................................................ 623/3.13
See application file for complete search history.

(56) References Cited

U.S. PATENT DOCUMENTS

| 5,300,111 | A | 4/1994 | Panton et al. |
|---|---|---|---|
| 5,443,503 | A | 8/1995 | Yamane |
| 5,674,281 | A | 10/1997 | Snyder |
| 8,608,798 | B2 | 12/2013 | Wampler |
| 2007/0253842 | A1 | 11/2007 | Horvath et al. |
| 2011/0144744 | A1 | 6/2011 | Wampler |

OTHER PUBLICATIONS

Korean Intellectual Property Office, international search report and written opinion issued on Aug. 2, 2011, related PCT Application No. PCT/US2010/058963, including application and claims searched, pp. 1-41.
Notice of allowance dated Aug. 19, 2013 for U.S. Appl. No. 12/960,129.
Notice of allowance dated Sep. 26, 2013 for U.S. Appl. No. 12/960,129.
Office action dated Jun. 6, 2012 for U.S. Appl. No. 12/960,129.

*Primary Examiner* — Thomas J Sweet
*Assistant Examiner* — Matthew Schall
(74) *Attorney, Agent, or Firm* — Wilson Sonsini Goodrich & Rosati

(57) ABSTRACT

A total artificial heart having a rotor with an impeller, wherein the rotor is mounted within a pump housing on a hollow shaft. The rotor is magnetically driven to produce rotary motion of the impeller for pumping blood. The motor is disposed within the pump housing such that axial translation within the housing acts as a shuttle valve to alternate flow between pulmonary and systemic circulation.

13 Claims, 6 Drawing Sheets

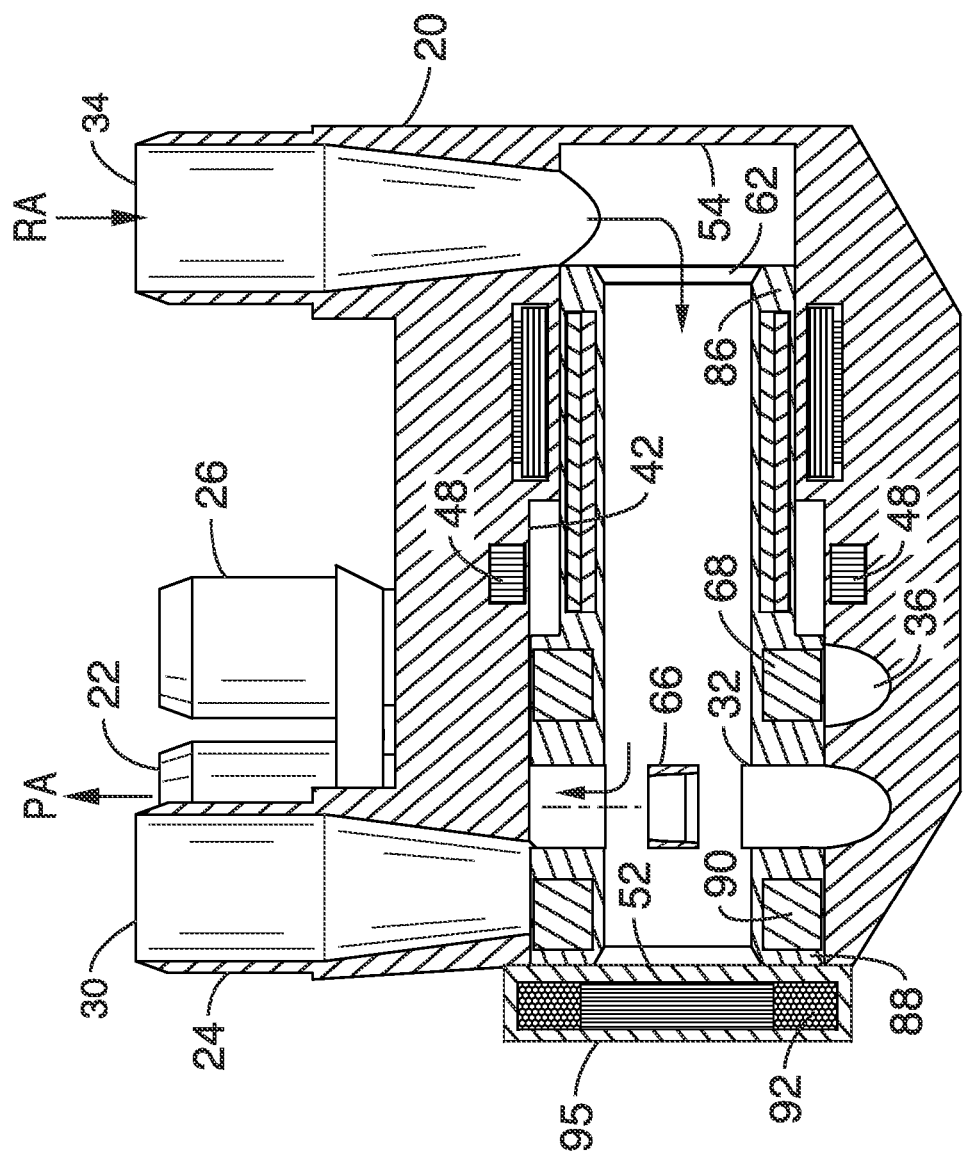

TOTAL ARTIFICIAL HEART

CROSS-REFERENCE TO RELATED APPLICATIONS

This application is a continuation of U.S. patent application Ser. No. 12/960,129 filed on Dec. 3, 2010, now U.S. Pat. No. 8,608,798, incorporated herein by reference in its entirety, which is a nonprovisional of U.S. provisional patent application Ser. No. 61/266,405 filed on Dec. 3, 2009, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to cardiovascular implants, and more particularly to devices that completely replace a failing heart to provide blood flow to the pulmonary and systemic circulation.

2. Description of Related Art

Congestive heart failure is a major, rapidly growing public health problem that results in hundreds of thousands of deaths annually. Patients with bi-ventricular end stage heart failure who are refractory to medications, surgical intervention and resynchronizer pacing are best treated with cardiac transplantation. However, donor hearts are limited to about 2,000 per year in the United States and, consequently, there is a large unmet need for approximately 75,000 patients who would benefit from cardiac transplantation, but for whom no donor heart is available. A mechanical total artificial heart (TAH) could replace a failing heart and offer improved survival and functional capability comparable to cardiac transplantation.

Extensive research since the mid 1960's has resulted in numerous left ventricular assist devices (LVAD) intended to take over part or all of the work of the left ventricle while working in parallel with the native heart. The HeartMate™, is a positive displacement pump used as a bridge to cardiac transplantation and destination therapy in patients with severe congestive heart failure. Most recently, the HeartMate™ II, a rotary pump, has received PMA approval for bridge to transplantation. LVAD's such as these are gaining clinical acceptance, but development of total artificial hearts (TAH) has not kept pace, particularly for permanent assistance without intention to bridge to cardiac transplantation. Two total artificial hearts are clinically available on a very limited basis in the United States.

The SynCardia TAH by CardioWest is implanted in the chest and is powered by an external pneumatic driver via air hoses which penetrate the chest. It has been approved for temporary use as a bridge to transplantation in patients who cannot be supported with an LVAD alone and has demonstrated clinical efficacy in several hundred patients. The Abiocor™ TAH by Abiomed, Inc. is intended for permanent use and is totally implantable. It has a self-contained electric motor and receives power by means of transcutaneous power transmission, but has been approved by FDA only for compassionate use.

Each of the CardioWest and Abiocor devices employ two separate pumps to replace the right and left ventricles, respectively. These pumps are positive displacement pumps with two valves per pump (total of four valves) to ensure unidirectional flow of blood. The anatomical compatibility of these devices has limited their use to larger patients, since positive displacement pumps are inherently large.

Rotary blood pumps based on centrifugal or axial flow hydraulics have proven to be safe and durable pumps for use as left ventricular devices and could offer many advantages over positive displacement pumps if they were adapted for use as a total artificial heart. Most importantly, rotary blood pumps would be much smaller than existing pulsatile TAH's and would not require artificial valves or a means for volume compensation or venting. In addition, rotary blood pumps, such as the HeartMate II, have proven durability for many years.

To date, all total artificial hearts employ two pumps whether they are positive displacement type or rotary pumps. All of the TAH's based on rotary blood pumps integrate the right and left heart pumps into a single housing which is an improvement over the use of two separate pumps.

A total artificial heart based on a single rotary impeller would offer significant advantage in reduced size, simplicity and cost over existing devices intended for complete replacement of the heart.

BRIEF SUMMARY OF THE INVENTION

The present invention is a total artificial heart (TAH) employing a single impeller that is capable of providing circulation to both the pulmonary (right) and systemic (left) circulation. A rotor has an impeller mounted on a hollow shaft which contains magnets that react with electrical coils in a housing to produce rotary motion for pumping and axial translation within the housing to shuttle flow between the right and left circulation. The flow produced is inherently pulsatile.

The present invention, according to certain aspects, provides a total artificial heart capable of completely supporting the pulmonary and systemic circulation of the body with a rotary blood pump utilizing only one impeller.

One aspect of the present invention provides a device comprising a rotary pump housing having a bore surrounded by a motor stator. Four connectors of the housing have apertures/channels that are in continuity with the bore and provide inflow and outflow for the right and left circulation. A rotor consists of a hollow shaft on which is mounted an impeller. Motor rotor magnets are located in the wall of the hollow shaft. During operation the rotor rotates within the housing and is capable of shuttling axially within the housing. The rotor is placed in the bore of a pump housing. Electrical coils surrounding the bore interact with the magnets in the rotor to produce rotary motion to pump fluid and axial motion to alternately pump blood between the pulmonary and systemic circulation.

The inflow to the impeller can be provided from either end of the hollow shaft. The rotor also acts as shuttle valve by translating along the axis of the pump housing and alternately exposing and covering the ports of the housing to provide flow to the right and left heart. A motor stator, concentric to the bore of the housing surrounds the motor rotor magnet in the hollow shaft. Current in the stator windings interacts with the magnetic field to produce torque and rotation of the rotor, thereby turning the impeller. As the rotor assembly translates axially, the outlet of the impeller is alternately directed to the right and left circulation via the arterial ports in the housing. Likewise, the bore of the rotor receives blood from the right and left atria through the atrial ports.

Balance of right and left flow can be achieved by adjusting the duty cycle or dwell time of the right versus the left side. Speed could also be simultaneously adjusted to provide additional control. Since the rotor is alternately pumping to the right and left side, the flow will be inherently pulsatile.

Radial support of the rotor will be provided by the action of a hydrodynamic bearing between the surface of the housing bore and the outer surface of the rotor wherein blood will be the hydrodynamic fluid. Internal pressure gradients will provide leakage flow within the journal bearing clearances to prevent stagnation and thrombus formation. Axial constraint of the rotor will be a combination of a passive axial magnetic bearing and hydrodynamic thrust bearings.

Connections to the vascular system will be accomplished with a combination of prosthetic arterial grafts and synthetic atrial cuffs. Power can be provided by means of a percutaneous wire or transcutaneous power transmission. Measurements of flow and or pressure will be used to control the duty cycle and dwell time of the rotor in order to balance the flow between the right and left sides of the circulation.

An aspect of the invention is total artificial heart (TAH) employing a single impeller that is capable of providing circulation to both the pulmonary (right) and systemic (left) circulation.

In one embodiment, the total artificial heart comprises a rotor having an impeller mounted on a hollow shaft which contains magnets that react with electrical coils in a housing to produce rotary motion for pumping and axial translation within the housing to shuttle flow between the right and left circulation.

In another embodiment, the total artificial heart comprises a rotary pump housing having a bore surrounded by a motor stator the housing having four connectors that are in continuity with the bore and provide inflow and outflow for the right and left circulation. The rotor generally comprises a hollow shaft on which is mounted an impeller; and wherein motor rotor magnets are located in a wall of the hollow shaft. During operation, the rotor rotates within the housing and is capable of shuttling axially within the housing.

In another embodiment, a rotor is placed in a bore of a pump housing; with a plurality of electrical coils surrounding the bore and which interact with magnets in the rotor to produce rotary motion to pump fluid and axial motion to alternately pump blood between pulmonary and systemic circulation.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 6 shows an axial section through the of FIG. 1 total artificial heart showing the rotor in position to pump from the right atria to the pulmonary artery.

DETAILED DESCRIPTION OF THE INVENTION

Referring more specifically to the drawings, for illustrative purposes the present invention is embodied in the apparatus generally shown in the figures. It will be appreciated that the apparatus may vary as to configuration and as to details of the parts.

Figure 1:
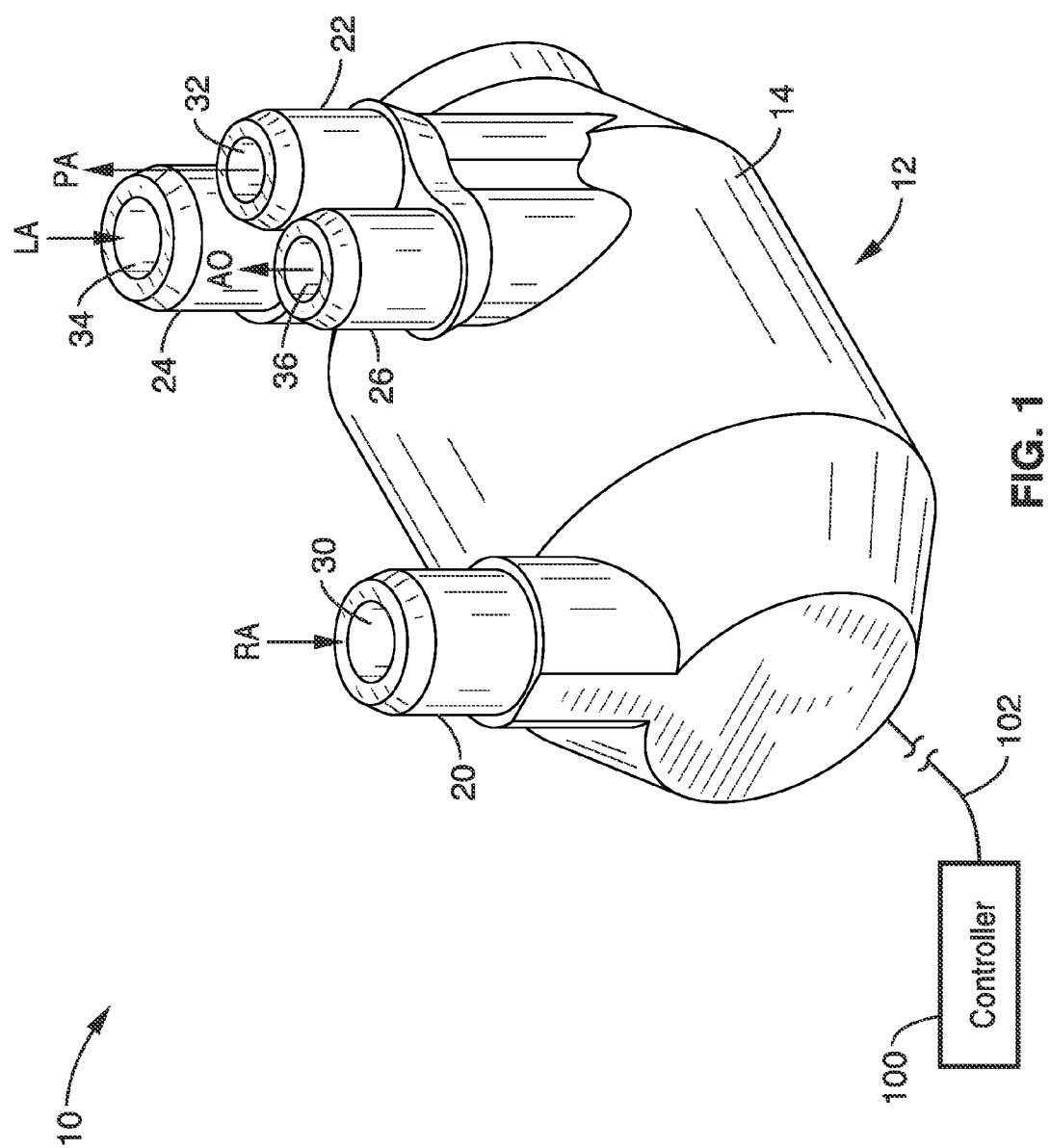
FIG. 1 shows an exterior isometric view of a total artificial heart, illustrating vascular connections for fluid access to the right and left atria and pulmonary artery and aorta.

FIG. 1 illustrates an exterior view of a total artificial heart (TAH) 10 in accordance with the present invention. TAH 10 comprises a pump housing 12 having a body 14 and four vascular connectors for accessing the circulatory system. The TAH 10 of the present invention is shown and illustrated in the description below for replacement of the left and right ventricles of the heart, while connecting for input from both the systemic venous circulation and the pulmonary venous circulation via the right and left atria (not shown). However, it is appreciated the venous and arterial blood input into the TAH 10 may be from any location along the venous or arterial circulatory systems.

As shown in FIG. 1, venous blood from the right atrium (RA) is directed into the TAH 10 via channel/aperture 30 of the RA connector 20. Oxygenated blood from the left atrium (LA) is directed into the TAH 10 via channel 34 of the LA connector 24. Venous blood is delivered to the pulmonary artery (PA) via channel 32 the PA connector 22. Arterial blood is delivered to the aorta (A0) via channel 36 of the AO connector 26.

Prosthetic conduits (not shown), such as arterial grafts, synthetic atrial cuffs, or the like, may be used to couple the connectors 20, 22, 24, and 26 to respective anatomical features the vascular system. Connectors 20, 22, 24, and 26 comprise cylindrical outer surfaces that are sized to provide purchase for an internal wall (not shown) of the lumen (or prosthetic conduit) to be connected with, and additional clamping means (not shown) may be used to seal the lumen with respect to the corresponding connector.

The displaced volume of the TAH 10 is preferably small enough such that the cavity left by removal of the native heart will be sufficient to accommodate the device. Ideally, TAH 10 will have a volume of less than 150 cc.

Power, control, and sensing feedback for the pump are provided via controller 100 and lead 102. The components of the controller may be external to the patient, or subcutaneous. For example, the controller 100 may comprise a processor and battery power source that are completely implanted within the body, such that the battery is recharged via transcutaneous energy transmission (TET) through the skin. Alternatively, the lead bundle 102 may lead through the skin to an external controller 100 and power supply. In yet another embodiment, one or more components providing power, control or sensing are a combination of both internal and external devices.

Figure 2:
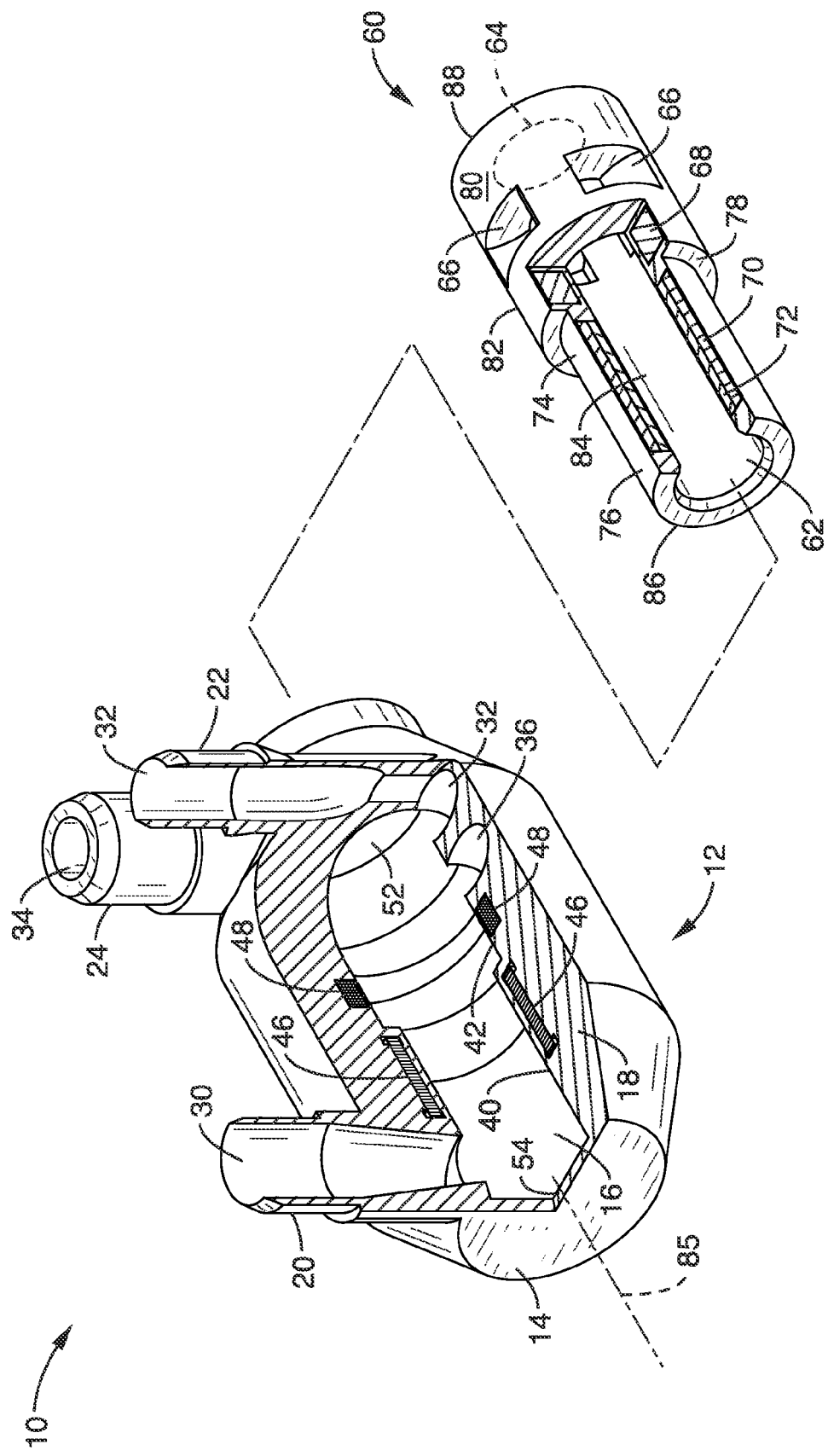
FIG. 2 shows an exploded isometric cut away view of a pump housing and a rotor of the total artificial heart shown in FIG. 1.

Referring now to FIG. 2, TAH 10 comprises a pump housing assembly 12 having a housing 14 configured to suspend a moveable rotor assembly 60 within inner chamber 16. The rotor assembly 60 comprises a rotor shaft 74 coupled to impeller body 82, which includes an impeller 66 comprising a plurality of radial slots that are in communication with a central channel 84 of the rotor assembly 60. The central channel 84 comprises a bore that passes through the entirety of the impeller assembly 60 from left inlet 62 at the left end 86 to right inlet 64 at right end 88. The bore 84 serves to channel blood into the hollow rotor 60 to the impeller 66.

The impeller assembly 60 is configured to be magnetically driven to rotate inside chamber 16 of the housing assembly 12. The rotor shaft 74 of the impeller assembly 60 comprises a cylindrical rotor magnet 70 surrounded by a backiron 72 are positioned within the wall of the rotor shaft 74.

The bore 16 of pump housing 14 comprises a stepped cylindrical channel in communication with input channels 30, 34 and output channels 32 and 36. The bore 16 comprises a first cylindrical inner surface 40 configured to interface with the cylindrical outer surface 76 of the rotor shaft 74, and a second inner cylindrical surface 42 configured to interface with the outer surface 80 of the impeller body 82. The left end 52 of the housing 14 comprises a cap 95 (see FIGS. 5 and 6) that may be detached from the housing 14 to allow insertion of the rotor 60. Cap 95 may be threaded into the housing 14, or may be attached by other means, such as welding, clamping, or the like.

Housing 14 comprises an annular motor stator 46 that surrounds the bore 16 at inner surface 40 such that the rotor stator 46 and is axially aligned with the rotor magnet 70 when the rotor assembly 60 is positioned within cavity 16. The motor stator 46 is concentric to the bore 16 of the housing and surrounds the motor rotor 60 magnet when positioned in the bore 16. Current in the stator 46 windings generates a magnetic field to interact with the rotor magnet 70 to produce torque and rotation of the rotor 60 about axis 85, thereby turning the impeller 66 to induce fluid flow.

While the stepped rotor configuration (e.g. smaller diameter shaft 74 and larger diameter impeller body) shown in FIGS. 2 through 5 is preferred, it is also appreciated that the rotor assembly may comprise a constant outer diameter across its length (not shown). Correspondingly, the inside diameter of the internal chamber 16 would also be constant.

Rotor assembly 60 also comprises an annular solenoid magnet 68 disposed within the wall of the impeller body 82. A solenoid coil 48 is disposed within the housing 14 to surround the housing bore 16 at surface 42, and is located to be proximate to the solenoid magnet 68 in the impeller body 82 when the rotor assembly 60 is positioned within cavity 16.

Figure 3:
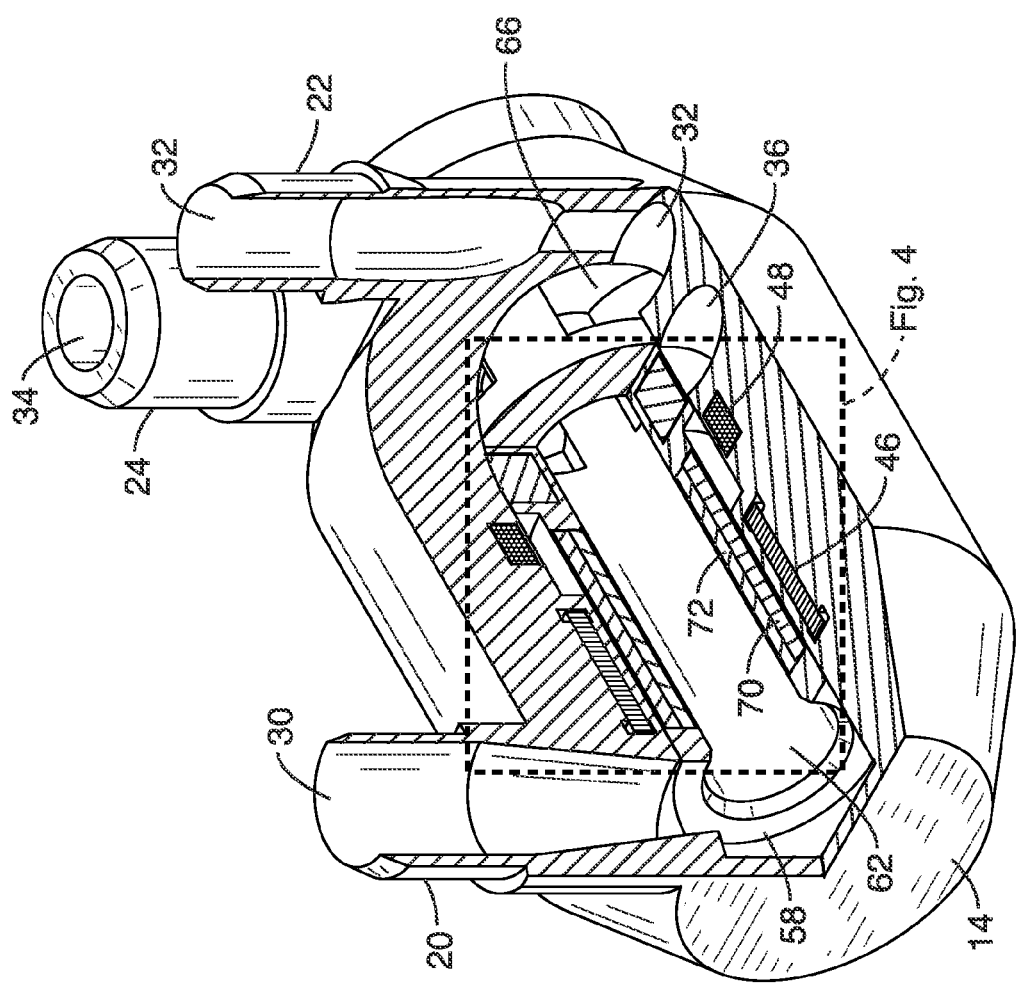
FIG. 3 illustrates an isometric cut away of the assembled total artificial heart of FIG. 1.
Figure 4:
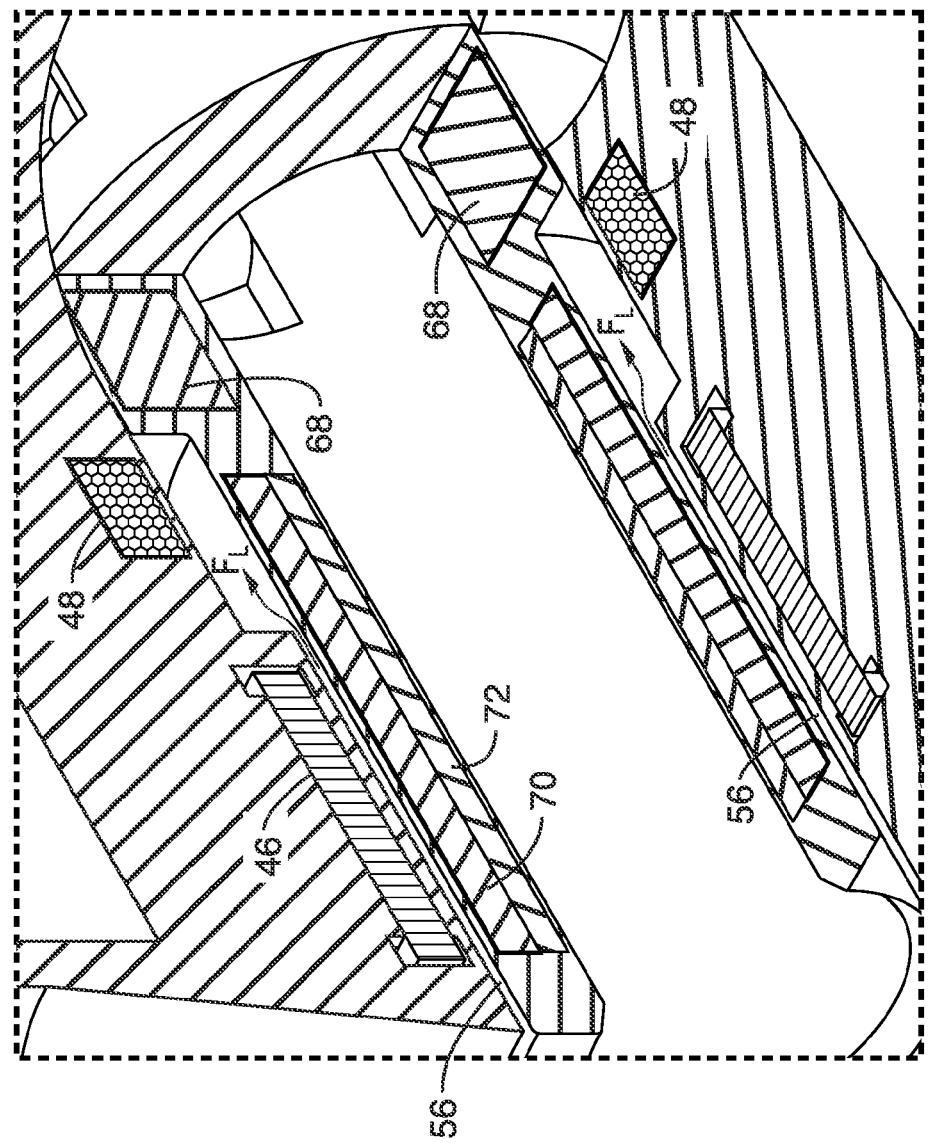
FIG. 4 shows a close-up view of the isometric cut away illustrated in FIG. 3.

FIGS. 3 and 4 illustrate a cutaway view of the pump assembly 10 rotor assembly 60 is positioned within cavity 16 of the housing assembly 12. During operation, the interaction between an electric current supplied to the motor stator 46 and the rotor magnet 70 produces rotary motion in the rotor 60 and hence, the impeller 66. The rotary motion of the impeller 66 imparts kinetic energy to the blood and creates pressurized flow to either the pulmonary artery (PA) or aorta (AO) while drawing blood from the RA and LA, respectively.

A hydrodynamic journal bearing action is created in bearing clearance 56 between one or more of the inner surfaces 42, 44 of the housing bore 16 and the outer surfaces 76, 80 of the rotor shaft 74 and impeller body 82. Thus, the diameter inner surfaces 42, 44 of the housing bore are generally in the range of 0.002 in.-0.020 in. and preferably within the range of 0.004 in.-0.008 in. larger than the diameters of the outer surfaces 76, 80 of the rotor shaft 74 and impeller body 82, respectively. Accordingly, the gap/clearance 56 shown in FIG. 4 is exaggerated for clarity. The hydrodynamic bearing supports the rotor assembly 60 radially within the housing. The bearing clearance 56 also serves as a leak path to allow the flow $F_L$ of blood through the clearance to remove heat and minimize the risk of clotting. Internal pressure gradients generated by the impeller provide leakage flow $F_L$ within the journal bearing clearances 56 to prevent stagnation and thrombus formation. Shear in this region is preferably below 1000 pascals to minimize the risk of blood damage. It is appreciated that either or both surfaces 42 and 44 may have a gap with respective surfaces of the housing that forms a hydrodynamic bearing.

For example, the radial gap between surface 42 of the housing and surface 82 of the of the impeller body may be sufficiently small (e.g. 0.002 in) to form a hydrodynamic bearing, while the rotor shaft outer surface 76 may have a significantly larger gap (e.g. 0.020 in or more) that is not a hydrodynamic journal bearing, and vise versa.

At least one hydrodynamic thrust bearing on either end of the rotor provides axial support for the rotor. Additional axial support is provided by the passive magnetic attraction between the motor stator 46 and the rotor magnet 70.

The rotor assembly 60 is configured to also act as a shuttle valve by translating along the axis 85 of the pump housing 14 and alternately exposing and covering the ports 30, 32, 34, and 36 of the housing 14 to provide flow to the right and left heart. Accordingly, the rotor assembly 60 is configured to have two configurations to alternate flow between the systemic and pulmonary circulatory systems. As the rotor assembly 60 translates axially along axis 85, the outlet of the impeller 66 is alternately directed to the right and left circulation via the arterial ports 32, 36 in the housing. Likewise, the central channel 84 of the rotor 60 receives blood from the right and left atria through the atrial ports 30, 34.

Figure 5:
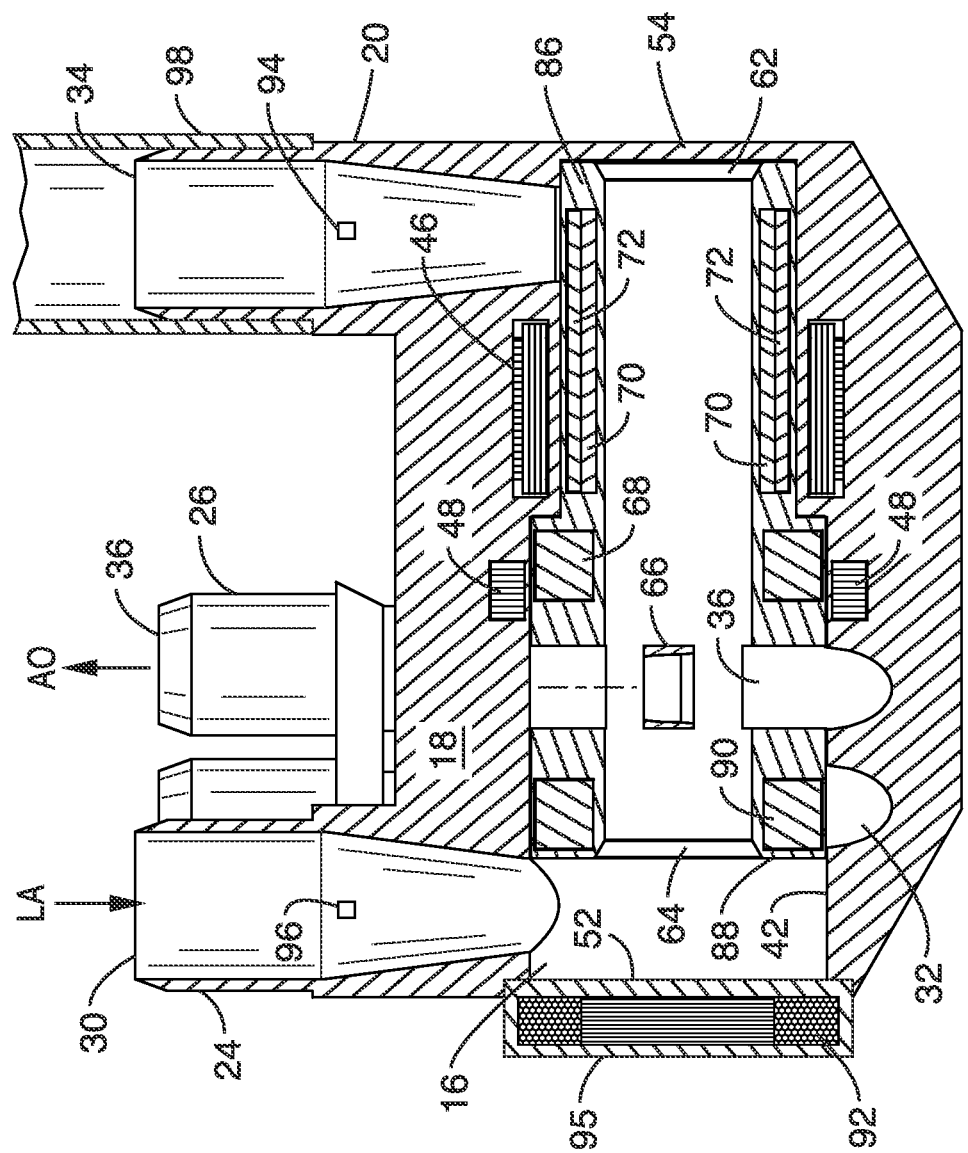
FIG. 5 shows an axial section through the total artificial heart of FIG. 1 showing the rotor in position to pump from the left atrium to the aorta.

FIG. 5 illustrates the system 10 in a first configuration (systemic circulation) that draws saturated blood from the left atrium (LA) and pumps it to the aorta (AO). In FIG. 5, the right side 86 of the rotor assembly 60 is positioned to the right side 54 of the pump housing 14 by the action of electrical current in solenoid coils 48, 92 acting on solenoid magnets 90, 68. Access to the input chamber 30 of the RA connector 20 (and right atrium connector 98) and output chamber 32 of the PA connector 22 are blocked by the solid surfaces 76, 80 of the rotor shaft 74 and impeller body 82 respectively. Accordingly, blood enters the input 34 of the LA connector 24, passes through inlet 64 of the rotor 60 and into the rotor central channel 84. The blood exits through the impeller 66 and into the output chamber 36 of the AO connector 26 into the aorta.

FIG. 6 illustrates the system 10 in a second configuration (pulmonary circulation) that draws desaturated blood from the right atrium (RA) and pumps it to the pulmonary artery (PA). Then the direction of the current in solenoid coils 94 and 48 is reversed, the magnetic field acts on the poles of the solenoid magnets 68, 90 to push the rotor axially along axis 85 of bore 16 in the opposite direction, translating the left end 88 of the rotor 60 to abut to the left end 52 of the chamber 16. In this position, the input channel 34 of the LA connector 24 and the output channel 36 of the AO connector 26 are blocked by the solid surfaces 76, 80 of the rotor shaft 74 and impeller body 82 respectively. In this rotor position, blood from the RA enters input 30 of the RA connector 20, passes through inlet 62 of the rotor 60, flows through central channel 84 and out the impeller 66 and into the output channel 32 of the PA connector 22 to the PA.

While the preferred embodiment uses both solenoids 92 and 48 acting on magnets 68 and 90, it is appreciated that only one of the solenoid/magnet pairs be necessary to drive axial or shuttling motion of the rotor 60. For example, solenoid 92 may be configured to generate an alternating attractive and repulsive force on magnet 90 to singly drive the axial shuttling motion of the rotor assembly 60. Alternatively, a biasing member (e.g. mechanical spring, magnetic spring, or the like—not shown) may be positioned on one side of the chamber to bias the rotor in one position, whereas the solenoid 92 acts to alternate between an "on" and "off" mode that drives the axial position of the rotor 60 against the biasing force applied by the biasing member.

Balancing of the flow between the pulmonary and systemic circulation is adjusted by controlling the dwell time or duty cycle of the impeller as it moves, alternately, back and forth in the pump housing.

Referring back to FIG. 1, controller 100 for driving the pump 10 may be based on sensorless commutation, which obviates the need for brushes, shaft seals and optical sensors. The control of flow balance between the pulmonary and systemic circulation may be supported via feedback from one or more sensors (e.g. sensors 94 and 96 illustrated in FIG. 5), with closed loop logic to insure that physiologic pressures are maintained in the atria. Direct measurement of blood flow may be performed with ultrasonic transducers 94 and 96 disposed in atria chambers 30, 32 that use the Doppler affect to measure velocity across a known cross sectional area (e.g. the diameter of the atrial chambers 30, 32). Signals from the transducers 94 and 96 are fed to controller 100, where they are processes with an algorithm that compares the right and left flows and adjust the dwell times to compensate for any disparity in flow.

Other velocity measuring technologies, such as hot wire anemometry or pitot tube, may also be adapted within the pump. Alternatively, pressures of the atria could be measured and these signals used to determine the ratio of the dwell time of the impeller 60 between the pulmonary and systemic circulation.

As an example, if the pressure of the left atrium 34 is too high, the dwell time on the pulmonary outlet 32 of the pump could be decreased, or the dwell time on the systemic outlet 36 increased. In either case, the ratio of the dwell time systemic/pulmonary would increase. Indirect measurements of atrial pressure can be accomplished by measuring the diameter of the atria or stretching of the atrial walls. Miniature ultrasonic transducers can be used for these measurements, and are stable when implanted.

By using measured parameters such as pressure, flow, flow velocity or oxygen saturation, it is possible for the pump 10 to adapt to any patient during a wide range of conditions at any time.

Accordingly, it will be appreciated that the present invention can be embodied in various ways which include, but are not limited to:

1. A total artificial heart, comprising: a pump housing comprising first, second, third and fourth vascular connectors; wherein each of the vascular connectors are in fluid communication with a bore within the housing; and a rotor configured to be rotatably housed within the bore; the rotor having an impeller configured to pump blood to and from the vascular connectors upon rotation of the rotor about a central axis of the bore; wherein the rotor is responsive to magnetic forces imparted from said pump housing to drive rotation of the rotor; wherein the rotor is configured to translate along the central axis of the bore from a first position to a second position; wherein in the first position, the rotor is configured to draw a first volume of blood from the first vascular connector and pump the first volume of blood into the second vascular connector; wherein in the second position, the rotor is configured to draw a second volume of blood from the third vascular connector and pump the second volume of blood into the fourth vascular connector.

2. A total artificial heart as recited in embodiment 1: wherein in the first position, the rotor is configured to block flow to and from the third and fourth vascular connectors; and wherein in the second position, the rotor is configured to block flow to and from the first and second vascular connectors.

3. A total artificial heart as recited in embodiment 1: wherein the first vascular connector comprises a left atrium (LA) connector, the second vascular connector comprises an aorta (AO) connector, the third vascular connector comprises a right atrium (RA) connector, the fourth vascular connector comprises a pulmonary artery (PA) connector; and wherein the rotor shuttles between the first position and the second position to alternate the output flow between systemic and pulmonary circulation.

4. A total artificial heart as recited in embodiment 3, wherein the first volume of blood is output into arterial circulation, and the second volume of blood is input from venous circulation.

5. A total artificial heart as recited in embodiment 1, further comprising: a motor stator disposed within the pump housing; and a first magnet disposed within the rotor; wherein the first magnet is responsive to a magnetic field generated by said motor stator to drive rotation of said rotor about said central axis.

6. A total artificial heart as recited in embodiment 5, further comprising: a solenoid disposed within the pump housing; and a second magnet disposed within the rotor; wherein the second magnet is responsive to a magnetic field generated by said solenoid to drive axial translation of said rotor from the first position to the second position.

7. A total artificial heart as recited in embodiment 6, further comprising: a controller coupled to the rotor stator; wherein the controller is configured to control the current delivered to the rotor stator to vary the speed of rotation of the rotor.

8. A total artificial heart as recited in embodiment 7: wherein the controller is coupled to the solenoid; wherein the controller is configured to control the current delivered to solenoid vary the duty cycle or dwell time between the first position and second position of the rotor.

9. A total artificial heart as recited in embodiment 2: wherein the impeller comprises a plurality of radial ports in communication with a central channel of the rotor; the central channel running axially through the rotor to form a first inlet at a first end of the rotor and a second inlet at a second end of the rotor.

10. A total artificial heart as recited in embodiment 9: wherein in the first position, the first inlet of the rotor is open to fluid communication with a first port coupled to the first vascular connector and the impeller is open to fluid communication with a second port coupled to the second vascular connector such that rotation of the impeller draws the first volume of blood from the first port and pumps the first volume of blood into the second port.

11. A total artificial heart as recited in embodiment 10: wherein in the second position, the second inlet of the rotor is open to fluid communication with a third port coupled to the third vascular connector and the impeller is open to fluid communication with a fourth port coupled to the fourth vascular connector such that rotation of the impeller draws the second volume of blood from the third port and pumps the second volume of blood into the fourth port.

12. A total artificial heart as recited in embodiment 10: wherein in the first position, an outside surface of the rotor is configured to block flow to and from the third and fourth ports.

13. A total artificial heart as recited in embodiment 11: wherein in the second position, an outside surface of the rotor is configured to block flow to and from the first and second ports.

14. An apparatus for implantation into the body of a patient, comprising: a pump housing comprising a plurality of vascular connectors; the plurality of connectors comprising a left atrium (LA) connector configured to be coupled to the LA of the patient, an aorta (AO) connector configured to be coupled to the AO of the patient, a right atrium (RA) connector configured to be coupled to the RA of the patient, and a pulmonary artery (PA) connector configured to be coupled to the PA of the patient; wherein each of the vascular connectors are in fluid communication with a bore within the housing; and a rotor configured to be rotatably housed within the bore; the rotor having an impeller configured to pump blood to and from the vascular connectors upon rotation of the rotor about a central axis of the bore; wherein the rotor is responsive to magnetic forces imparted from said pump housing to drive rotation of the rotor; wherein the rotor is configured to translate along the central axis of the bore from a first position to a second position; wherein in the first position, the rotor is configured to draw a first volume of blood from the LA and pump the first volume of blood into the AO; wherein in the second position, the rotor is configured to draw a second volume of blood from the RA and pump the second volume of blood into the PA; wherein the rotor the rotor is configured to shuttle between the first position and the second position to alternate the output flow between systemic and pulmonary circulation.

15. An apparatus as recited in embodiment 14: wherein in the first position, the rotor is configured to block input flow from the RA and output flow to the PA; and wherein in the second position, the rotor is configured to block input flow from the LA and output flow to the AO.

16. An apparatus as recited in embodiment 14, further comprising: a motor stator disposed within the pump housing; and a first magnet disposed within the rotor; wherein the first magnet is responsive to a magnetic field generated by said motor stator to drive rotation of said rotor about said central axis.

17. An apparatus as recited in embodiment 16, further comprising: a solenoid disposed within the pump housing; and a second magnet disposed within the rotor; wherein the second magnet is responsive to a magnetic field generated by said solenoid to drive axial translation of said rotor from the first position to the second position.

18. An apparatus as recited in embodiment 17, further comprising: a controller coupled to the rotor stator; wherein the controller is configured to control the current delivered to the rotor stator to vary the speed of rotation of the rotor.

19. An apparatus as recited in embodiment 18: wherein the controller is coupled to the solenoid; wherein the controller is configured to control the current delivered to solenoid to vary the duty cycle or dwell time between input from the LA and the RA.

20. An apparatus as recited in embodiment 14: wherein the impeller comprises a plurality of radial ports in communication with a central channel of the rotor; the central channel running axially through the rotor to form a first axial inlet at a first end of the rotor and a second axial inlet at a second end of the rotor.

21. An apparatus as recited in embodiment 20: wherein in the first position, the first axial inlet of the rotor is open to fluid communication with a first port coupled to the LA connector and the impeller is open to fluid communication with a second port coupled to the AO connector such that rotation of the impeller draws the first volume of blood from the first port and pumps the first volume of blood into the second port.

22. An apparatus as recited in embodiment 21, wherein in the second position, the second axial inlet of the rotor is open to fluid communication with a third port coupled to the RA connector and the impeller is open to fluid communication with a fourth port coupled to the PA connector such that rotation of the impeller draws the second volume of blood from the third port and pumps the second volume of blood into the fourth port.

23. The total artificial heart of embodiment 21, wherein in the first position, an outside surface of the rotor is configured to block flow to and from the third and fourth ports.

24. The total artificial heart of embodiment 22, wherein in the second position, an outside surface of the rotor is configured to block flow to and from the first and second ports.

25. An apparatus as recited in embodiment 19, further comprising: one or more sensors coupled to the controller; wherein the one or more sensors are configured to acquire data relating to a physiological measurement of the patient; wherein the controller is configured to vary said dwell times and rotation speed according to said data.

26. A total artificial heart, comprising: a pump housing comprising a plurality of vascular apertures; a rotor configured to be rotatably disposed within the pump housing; the rotor having an impeller configured to pump blood to and from the vascular apertures upon rotation of the rotor; wherein the rotor is configure to operate as a shuttle valve to alternate blood flow between the plurality of vascular apertures.

27. A total artificial heart as recited in embodiment 26: wherein the rotor is configured to translate within said housing to switch flow between the vascular apertures.

28. A total artificial heart as recited in embodiment 27: wherein the rotor is configured to translate along an axis of rotation of the rotor.

29. A total artificial heart as recited in embodiment 28: wherein the rotor is configured to translate from a first position to a second position; wherein in the first position, the rotor is configured to receive a first volume of blood from a first vascular aperture and pump the first volume of blood into a second vascular aperture; and wherein in the second position, the rotor is configured to receive a second volume of blood from a third vascular aperture and pump the volume of blood into a fourth vascular aperture.

30. A total artificial heart as recited in embodiment 29: wherein in the first position, the rotor is configured to block input of blood flow from the third vascular aperture and output of blood flow to the fourth vascular aperture; and wherein in the second position, the rotor is configured to block input of blood flow from the first vascular aperture and output of blood flow to the second vascular aperture.

31. A total artificial heart as recited in embodiment 26: wherein the rotor comprises only one impeller.

While this invention has been described in conjunction with the specific embodiments outlined above, it is evident that many alternatives, modifications and variations will be apparent to those skilled in the art. For example, radial suspension of the rotor could be achieved with magnetic bearings, either passive or actively controlled. Likewise, active magnetic control in the axial direction could be adapted to this concept and numerous form factors for the outer surface and geometry of vascular connectors could be implemented to optimize anatomical placement.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for pumping blood in a patient comprising:
   providing a pump comprising a housing having an impeller rotatably and translatably housed within a bore of the housing;
   wherein the pump is configured to rotate the impeller in a first axial position to pump venous blood from venous circulation to a pulmonary circulation and to rotate the impeller in a second axial position to pump blood from a left atrium to arterial circulation.

2. A method as in claim 1, wherein the impeller is rotated in the first axial position to pump the blood from (a) a right atrium or vasculature leading to the right atrium to (b) a pulmonary artery while blocking flow from a left atrium to arterial circulation.

3. A method as in claim 2, wherein the impeller is rotated in the second axial position to pump the blood from (c) the left atrium to the aorta while blocking flow from the venous circulation to the pulmonary circulation.

4. A method as in claim 1, wherein the pump is fully implanted in the patient.

5. A method as in claim 1, wherein rotating comprises imparting magnetic forces from the pump housing to drive rotation of the rotor.

6. A method as in claim 1, wherein the rotor is configured to translate along the central axis of the bore from the first position to the second position.

7. A method as in claim 1, wherein in the first position, the rotor is configured to draw a first volume of blood from the right atrium through a first vascular connector and pump the first volume of blood through a second vascular connector to the pulmonary artery while blocking flow to and from a third and a fourth vascular connectors and wherein in the second position, the rotor is configured to draw a second volume of blood from the left atrium through the third vascular connector and pump the second volume of blood into aorta through the fourth vascular connector while blocking flow to and from the first and second vascular connectors.

8. A method for pumping blood in a patient comprising:
   implanting a pump comprising a housing having first, second, third and fourth vascular connectors, and an impeller rotatably and translatably mounted housed within a bore of the housing; and
   connecting the first vascular connector to a left atrium (LA), the second vascular connector to an aorta (AO), the third vascular connector to a right atrium (RA), and the fourth vascular connector to a pulmonary artery (PA);
   wherein the pump is configured to rotate the impeller in a first axial position to pump venous blood from the right atrium to the pulmonary artery and to rotate the impeller in a second axial position to pump blood from the left atrium to the aorta.

9. A method as in claim 8, wherein blood flow from the left atrium to the aorta is blocked when the rotor is in the first axial position.

10. A method as in claim 9, wherein blood flow from the right atrium to the pulmonary artery is blocked when the rotor is in the second axial position.

11. A method as in claim 8, wherein the pump is fully implanted in the patient.

12. A method as in claim 8, wherein rotating comprises imparting magnetic forces from the pump to drive rotation of the rotor.

13. A method as in claim 8, wherein the rotor is configured to translate along the central axis of the bore from the first position to the second position.

* * * * *